United States Patent [19]

Teeter

[11] Patent Number: 4,729,894

[45] Date of Patent: Mar. 8, 1988

[54] POULTRY DRINKING WATER ADDITIVE

[75] Inventor: Robert G. Teeter, Stillwater, Okla.

[73] Assignee: Oklahoma State University, Stillwater, Okla.

[21] Appl. No.: 722,001

[22] Filed: Apr. 11, 1985

Related U.S. Application Data

[63] Continuation-in-part of Ser. No. 567,507, Jan. 3, 1984, Pat. No. 4,608,257.

[51] Int. Cl.$^4$ .............................................. A61K 33/14
[52] U.S. Cl. .................................... 424/153; 424/127; 424/166
[58] Field of Search ........................................ 424/153

[56] References Cited

U.S. PATENT DOCUMENTS 4,182,755  1/1980  McNeff .............................. 424/166

OTHER PUBLICATIONS

McCormick et al.–Chem. Abst. vol. 92 (1980) p. 196, 709e.
Garlich et al.–Chem. Abst. vol. 94 (1981) p. 82, 624j.

Primary Examiner—Sam Rosen
Attorney, Agent, or Firm—Head & Johnson

[57] ABSTRACT

A method of reducing respiratory alkalosis (high blood pH) and enhancing productivity (rate of weight gain) in poultry during periods of chronic or acute heat stress (high heat and humidity) involving the steps of supplementing the birds' diet (feedstuffs and/or water) with acids (hydrogen ion donor) and bicarbonate donors ($NaHCO_3$) or supplementing the birds' drinking water with additional potassium ion (e.g. KCl or $K_2CO_3$) and/or ammonium chloride with or without $NaHCO_3$ and ascorbic acid. The addition of an acid donor as a poultry feed or water additive and the use of additional potassium in the drinking water significantly reduces the alkalosis induced mortality rate and enhances the rate of weight gain (up to 30 percent). By including $NaHCO_3$ in the feed ration, the rate of gain is further enhanced (an additional 9 percent). The further intention addition of a sodium free, chloride ion donor also promotes increased rate of gain. The use of a $H_2$ antagonist (cimetidine) to reduce stomach acid production is also beneficial to increase growth rate and mortality by reducing blood pH.

11 Claims, No Drawings

POULTRY DRINKING WATER ADDITIVE

CROSS-REFERENCE TO RELATED APPLICATION

This application is a continuation-in-part of application Ser. No. 567,507 filed Jan. 3, 1984, now U.S. Pat. No. 4,608,257.

BACKGROUND OF THE INVENTION

1. Field of the Invention

This invention relates to improved feedstuffs and/or water for poultry and methods for their use. More specifically, this invention relates to a poultry feed or water additive and dietary changes which alleviate respiratory alkalosis and associated increased mortality, decreased egg sheel thickness and decreased growth rate that occur during periods of severe heat stress.

2. Description of the Prior Art

It is generally known that poultry such as chickens, geese, turkeys, quail, pheasants and the like are particularly susceptible to poor productivity (reduced growth rate, feed efficiency, egg shell quality and high mortality) during periods of environmental heat stress (high temperatures and high relative humidity). Controversy exists in contemporary scientific literature regarding the occurrence of alkalosis in heat stressed birds and consequently, no therapeutic treatment for alkalosis founded or based on direct scientific evidence is available and to the best knowledge of the inventor, no direct knowledge of a poultry bicarbonate ion requirement during heat stress existed prior to the present invention.

It is known that heat stress substantially reduces the growth rate of broiler chicks. Diets have been altered to reduce this problem via reducing the heat increment of the diet with fat supplementation (H. L. Fuller et al; "Effect of Heat Increment of the Diet on Feed Intake and Growth of Chicks Under Heat Stress", Proc. Maryland Nutr. Conf., pp 58–64, 1973) and improved the amino acid balance (P. W. Waldroup et al; "Performance of Chicks Fed Diets Formulated to Minimize Excess Levels of Essential Amino Acids", Poultry Sci., 55: 243–253, 1976). It has also been suggested that the decline in growth rate results directly from reduced feed intake (R. L. Squibb et al; "Growth and Blood Constituents of Immature New Hampshire Fowl Exposed to Constant Temperatures of 99° for 7 Days", Poultry Sci., 38: 220–221, 1959). It has been demonstrated that the growth rate of heat stressed broilers can be increased by force feeding at a level exceeding ad libitum feed intake (M. O. Smith et al; "Feed Intake and Environmental Temperature Effects Upon Growth, Carcass Traits, Ration Digestibility, Digestive, Passage Rate and Plasma Parameters in Ad Libitum and Force-Fed Broiler Chicks" Poultry Sci., 62: 1504 abstr., 1983). It is also generally known that blood alkalosis precipitated through altering the Na/Cl ratio (S. Hurwitz et al; "Sodium and Chloride Requirements of Chick; Relationship to Acid-Base Balance", Poultry Sci., 52: 903–909, 1973) reduces both the feed consumption and growth rate of chicks; however, the studies were not thermal stress, per se.

At high ambient temperatures, evaporative cooling through panting is an important means of heat loss for fowl (G. M. Jukes, "Transport of Blood Gases", In: Physiology and Biochemistry of the Domestic Fowl, Vol. 1 Bell and Freeman, eds., Academic Press, N.Y., 1971). Hyperthermic panting has precipitated respiratory alkalosis (S. A. Richards; "Physiology of Thermal Panting in Birds", Ann. Biol. Anim. Biophys., 10: 151–168, 1970). However, respiratory alkalosis has not been consistently observed in fowl exposed to thermal stress. Parker et al ("Thermal Stress Effects on Certain Blood Characteristics of Adult Male Turkeys", Poultry. Sci. 50: 1287–1295, 1971) observed that the pH in the male turkey decreased when exposed to thermal stress, while Kohne et al ("Changes in Plasma Electrolyetes, Acid-Base Balance and Other Physiological Parameters of Adult Female Turkeys Under Conditions of Acute Hyperthermia", Poultry Sci., 54: 2034–2038, 1975) reported that acute hyperthermia produced profound alkalosis, but chronic hyperthermia ("Acid-Base Balance, Plasma Electrolytes and Production Performance of Adult Turkey Hens Under Conditions of Increasing Ambient Temperature", Poultry Sci., 54: 2038–2045, 1975) has no effect. Darre et al ("Time Course of Change in Respiratory Rate, Blood pH and Blood $pCO_2$ of SCWL Hens During Heat Stress", Poultry Sci., 59: 1598 abstr., 1980) observed that pH increased in a curvilinear fashion as leghorn hens were exposed to increasing ambient temperature changes. Siegel et al ("Blood Parameters of Broilers Grown in Plastic Coops and on Litter at Two Temperatures", Poultry Sci., 53: 1016–1024, 1974) found no difference in blood pH for broilers reared under continuous 35° C. versus thermoneutral conditions. This result agrees with Vo et al ("The Effect of High Temperatures on Broiler Growth", Poultry Sci., 54: 1347–1348 abstr. 1975), but contradicted the work of Bottje et al ("Effect of an Acute Heat Stress on Blood Flow in the Coeliac Artery of Hubbard Cockerels", Poultry Sci., 62: 1386–1387 abstr., 19832) wherein it was reported that blood pH was elevated. And, Parket et al ("Effect of Thermal Stress on Adult Male Turkeys", Poultry Sci., 49: 1425 str., 1970) reported that heat stress had no effect on blood pH other than the fact that pH was more variable among heat stressed birds than thermoneutral controls. Although the reasons for these discrepancies are not clear, they may include the degree of thermal stress, type of stress (acute versus chronic), blood collection site or the like and in view of the teachings of the present invention may involve the sampling time relative to the respiratory state of the birds. According to the present invention, it is observed that the birds exposed to chronic thermal stress exhibit a respiratory cycle of panting and non-panting phases which result in an oscillation between normal and alkalotic blood conditions.

SUMMARY OF THE INVENTION

In view of the prior art, I have discovered that poultry exposed to heat stress suffer from specific chemical imbalances which are most readily detectable in panting birds and which when corrected, increase poultry production. I have established that heat stressed poultry suffer from periodic or cyclic occurrences or bouts of blood alkalosis and bicarbonate ion deficiency. In view of these discoveries, I have developed a poultry feed and/or feedstuff additive/supplement and drinking water additive as well as methods of use for alleviating heat stress induced chemical imbalances in poultry.

Thus, the present invention provides a method of treating heat stress in poultry comprising the step of supplementing the diet of the poultry with from about 0.1 weight percent to about 3 weight percent of hydrogen ion donor. The present invention further provides a method of treating heat stress in poultry comprising the step of supplementing the diet of the poultry with about 0.5 weight percent of a bicarbonate ion donor. In specific embodiments of the present invention, the hydrogen ion donor is $NH_4Cl$ or HCl, the bicarbonate ion donor is $NaHCO_3$ and the sodium free, chloride ion donor is $CaCl_2$.

The present invention further provides a method of treating heat stress in poultry comprising the step of supplementing the diet of the poultry with poultry drinking water containing additional dissolved potassium ion and/or additional $NH_4Cl$. Preferably, this drinking water will contain from 0.05 weight of either supplement or mixture thereof up to 1.0 weight percent potassium (water soluble, non-toxic, potassium salt) or 0.6 weight percent $NH_4Cl$ or a mixture thereof within these upper limits. The invention further provides that the drinking water be further supplemented with 0.05 to 0.1 weight percent $NaHCO_3$ as well as small quantities of ascorbic acid.

It is an object of the present invention to provide a poultry raiser with a means of improving the productivity of birds raised during periods of heat and/or high relative humidity stress. It is a further object to provide a method and feed additive that will during period of heat stress significantly alleviate the problems of reduced growth rate, decreased feed efficiency, reduced egg shell thickness and increased mortality rate. It is an object of the present invention to provide a method and feed additive that will prevent heat stress induced respiratory alkalosis in poultry. Fulfillment of these objects and the presence and fulfillment of other objects will be apparent upon complete reading of the specification and claims contained herein.

DESCRIPTION OF THE PREFERRED EMBODIMENTS

According to the present invention, the previously observed reduced growth rate, feed efficiency, egg shell thickness and increased mortality rate for poultry and other birds during periods of heat stress caused by high temperatures or high temperatures and high humidity are related to chemical imbalances induced by or resulting from the heat stress. Specifically, according to the present invention, the occurrence of respiratory alkalosis is cyclic or oscillatory in that the increase in blood pH is in phase with the respiratory cycle of panting and non-panting phases of the heat stressed bird. In other words, the high blood pH, alkalosis, occurring during the panting stage of the heat stressed fowl returns to a more normal value for pH range upon cessation of panting. Thus, the blood pH in panting birds (e.g., pH=7.395 at 32° C.) drops back to a lower value (e.g., pH=7.28 at 32° C.) reminiscent of a non-panting normal value of a non-heat stressed bird (e.g., pH=7.28 at 24° C.). Acute thermal stress, obtained by quickly elevating ambient temperatures (e.g., from 32° to 41° C.) over a twenty minute period) creates an even further increase in blood pH (e.g., pH=7.521).

Further, according to the present invention, the heat stressed birds suffer from a bicarbonate ion deficiency which is also related to the reduced rate of weight gain even though the bicarbonate ion on an acid/base analysis would further promote alkalosis (i.e., unfavorable $pK_a$). Thus, according to the present invention, including 0.5% $NaHCO_3$ in the diet of birds subjected to chronic heat stress, enhances body weight gain even through it tends to increase blood pH in non-panting birds. Further, adding 0.3 up to 1% $NH_4Cl$ to diets decreases blood pH and increases body weight gain. The effects appear to be linear with respect to $NH_4Cl$ doses up to 1% $NH_4Cl$, but drop off as the dose approaches 3% $NH_4Cl$ and actually precipitate blood acidosis at these higher dosages. Supplementing a 1% $NH_4Cl$ diet with 0.5% $NaHCO_3$ results in a synergistic weight gain. Manipulating the sodium to chloride ratio by adding a sodium free chloride salt (e.g., $CaCl_2$) further increases body weight gain and slightly reduces the severity of alkalosis. Thus, according to the present invention, the blood alkalosis that limits growth rate of broiler chicks or the like reared under chronic thermal stress and the respiratory alkalosis and weight gain depression attributed to thermal stress can be partially alleviated by diet.

In order to explore and evaluate the concepts and features of the present invention, a series of experiments was performed using live chickens. Unless otherwise indicated, each experiment involved Arbor Acre x Vantress chicks which were fed a corn/soybean meal starter diet during the first four weeks post-hatching. On the first day of the fourth week, following an overnight fast, the chicks were weighed and randomly allotted to experimental groups (20 birds per treatment). The birds were individually housed for three weeks in 30.5×38.1 cm wire cages within thermostatically and humidistatically controlled chambers under continuous tungsten filament lighting. Week one was utilized to adapt all birds to test rations as follows:

| BASAL RATION COMPOSITION FOR EXPERIMENTS | | |
|---|---|---|
| Ingredient | Numerical[1] Name | % |
| Ground Corn Grain | 4-02-931 | 48.0 |
| Soybean meal (44%) | 5-04-604 | 35.0 |
| Corn oil | 4-07-822 | 6.0 |
| Meat + bone meal | 5-00-388 | 5.0 |
| Dicalcium Phosphate | 6-01-080 | 1.0 |
| Calcium Carbonate | 6-01-069 | .9 |
| Vitamin Mix | — | .5 |
| NaCl | 6-14-013 | .3 |
| DL-Methionine | — | .2 |
| Trace Mineral | — | .1 |
| Ground Polyethylene | — | 3.1 |

[1] Atlas of Nutritional Data on United States and Canadian Feeds and to increased chamber temperature (2.8 C./day) to 32° C. (80% relative humidity) for heat stress birds whicle control birds were maintained under thermoneutral condition of 24° C. (65% relative humidity). Feed and water were continuously available. Body weight gains and feed consumption were tallied weekly. All dietary additions were made at the expense of polyethylene. Where blood data are reported, blood was obtained via jugular venipuncture and pH was immediately analyzed utilizing a Corning blood pH/gas analyzer. Data were subject to analysis of variance using the General Linear Model of the statistical analysis system (A. J. Barr et al; "A User's Guide to SAS", Statistical Analysis System Institute, Inc., Carry, NC., 1976). The following EXAMPLES represent the specific experiments performed and the respective results.

EXAMPLE I

The purpose of this experiment was to measure blood pH of broiler chicks raised in thermoneutral and heat stressed environments. Sixty birds were assigned to three groups of twenty birds each of which the first two groups were subjected to the thermostressed environment. The blood pH, $CO_2$ and $HCO_3^-$ concentrations were determined on the last day of the experiment as follows: Group 1 while panting; Group 2 non-panting and Group 3 at random without regard to respiratory state. Twenty birds of Group 3 were assigned to the thermoneutral environment and bled at random since these birds did not pant. The results, (TABLE I), demonstrate that birds suffer from blood alkalosis only while panting which explains the confusion in the literature as heat stressed birds do not pant continuously. Additionally, the study demonstrates that heat stressed birds have lower blood concentrations of $CO_2$ and $HCO_3^-$ raising the possibility that they may respond to $CO_2$ and/or $HCO_3^-$ supplementation.

TABLE I

| Parameter | Thermoneutral | Heat Stress | Pooled SEM |
|---|---|---|---|
| Body wt. gain[a] (g) | 913[b] | 427[c] | 45 |
| Feed consumption[a] (g) | 2173[b] | 1123[c] | 62 |
| Blood pH | | | |
| Non-panting | 7.280[b] | 7.280[b] | — |
| Panting | — | 7.395[b] | .020 |
| Random | — | 7.309[b] | — |
| Blood $CO_2$ | | | |
| Non-panting | 18.6[b] | 9.1[c] | — |
| Panting | — | 5.9[c] | .81 |
| Random | — | 6.7[c] | — |
| Blood $HCO_3^-$ | | | |
| Non-panting | 8.14 | 3.3[c] | — |
| Panting | — | 4.8[c] | .73 |
| Random | — | — | — |

[a]Averaged across non-panting, panting and random pH sampling groups
[bc]Values within a major parameter with unlike superscripts differ (P < .05).

EXAMPLE II

The purpose of this experiment was to evaluate the potential of acids (hydrogen ion donors) as therapeutic agents to correct the periodic heat stress induced alkalosis. Ammonium chloride was utilized as the model hydrogen ion donor. The results (TABLE II), demonstrate that providing birds with supplemental hydrogen ions reduces the severity of alkalosis and significantly increases (P<0.05) growth rate. Caution must be utilized however, for too much acid can apparently cause blood acidosis and negate the beneficial effect.

TABLE II

| Treatment | Body Weight Gain (g) | | Feed Consumption (g) | | | Blood pH Hot | |
|---|---|---|---|---|---|---|---|
| | TN[a] | Heat Stress | TN[a] | Heat Stress | TN[a] | Non-panting | Panting |
| Basal diet | 933[b] | 442[d] | 2617[b] | 1949[d] | 7.290[c] | 7.294[c] | 7.381[b] |
| Basal diet + .3% $NH_4Cl$ | — | 484[dc] | — | 2011[dc] | — | 7.290[c] | 7.357[bc] |
| Basal diet + 1% $NH_4Cl$ | — | 553[c] | — | 2173[c] | — | 7.195[cd] | 7.305[bc] |
| Basal diet + 3% $NH_4Cl$ | — | 454[d] | — | 1958[dc] | — | 7.090[d] | 7.215[d] |

[a]Thermoneutral
[bcd]Values within a major heading classification with unlike superscripts differ (P < .05).

EXAMPLE III

This experiment was conducted to compare the potential of two hydrogen ion donors, $NH_4Cl$ and $HCl$, to demonstrate that more than one hydrogen ion donor may be utilized to correct the heat stress induced alkalosis. Results, (TABLE III), demonstrate that equal molar dietary additions of $HCl$ and $NH_4Cl$ increase growth rate but not to the same degree. The differing response is likely dependent upon the acid's anion content and its $pK_a$. The study also illustrates that supplemental hydrogen ions are of value during heat stress but not necessarily during growing periods exposing birds to more ideal temperature.

TABLE III

| Treatment | Body Weight Gain (g) | | Feed Efficiency | |
|---|---|---|---|---|
| | Thermo-neutral | Heat Stressed | Thermo-neutral | Heat Stressed |
| Poultry Ration | 978[a] | 423[a] | .41 | .37 |
| Poultry Ration + 1% $NH_4Cl$ | 872[b] | 597[b] | .38 | .38 |
| Poultry Ration + .68 $HCl$ | 798[c] | 572[b] | .38 | .38 |

[abc]Values within a heading classification with unlike superscripts differ (P < .05).

EXAMPLE IV

This experiment was conducted to determine the potential of manipulating the sodium/chloride ratio to reduce blood pH and thereby decrease the deleterious effects of heat stress induced alkalosis. Results, (TABLE IV), demonstrate that reducing the sodium to chlorine ratio tends to lower blood pH and enhance productivity but that the response is not as effective as adding a hydrogen ion donor.

TABLE IV

| Treatment | Body Weight Gain (g) | | Feed Consumption (g) | | | Blood pH Hot | |
|---|---|---|---|---|---|---|---|
| | TN[a] | Heat Stress | TN | Heat Stress | TN | Non-Panting | Panting |
| Basal Diet | 933[b] | 442[d] | 2617[b] | 1949[d] | 7.290[dc] | 7.294[dc] | 7.381[b] |
| Basal Diet + 1% $NH_4Cl$ | — | 553[c] | — | 2173[c] | — | 7.195[d] | 7.305[bc] |
| Basal Diet + .5% $CaCl_2$ | — | 481[cd] | — | 1945[d] | — | 7.330[bc] | 7.354[bc] |
| Basal Diet + 1.0% $CaCl_2$ | — | 474[d] | — | 1986[cd] | — | 7.256[dc] | 7.332[bc] |

[a]Thermoneutral
[bcd]Values within a major heading classification with unlike superscripts differ (P < .05).

EXAMPLE V

This experiment was conducted to determine the potential of utilizing drugs with the purpose of repartitioning the birds' existing hydrogen stores to increase blood hydrogen ion concentration and thereby reduce the deleterious effects of heat stress. The model drug chosen was cimetidine, a potent $H_2$ antagonist known for treatment of peptic ulcers and alkalosis by lowering blood pH. Drugs have the potential to repartition body hydrogen stores and consequently increase body weight gain and decrease mortality. Surprisingly, including cimetidine in the diet also reduced abdominal fat content which may also constitute a new application for this drug type.

TABLE V

|  | Heat Stress | | | | |
|---|---|---|---|---|---|
|  | Cimetidine Level (ppm) | | | | |
|  | Basal | 10 | 30 | 100 | 300 |
| Blood pH | $7.46^a$ | $7.42^{ab}$ | $7.39^{ab}$ | $7.31^b$ | $7.36^{ab}$ |
| Gain (g) | 407 | 400 | 414 | 420 | 439 |
| Mortality (%) | $64^a$ | $42^{bc}$ | $37^{bc}$ | $37^{bc}$ | $4.23^a$ |
| Proventriculus pH | $1.92^c$ | $2.41^{bc}$ | $2.289^{bc}$ | $3.05^{ab}$ | $4.23^a$ |
| Abdominal Fat | $1.80^a$ | $1.2^b$ | $1.2^b$ | $.98^b$ | $.94^b$ |

% body wt.
$^{abc}$Means within a row classification with unlike superscripts differ (P < .05).

EXAMPLE VI

Growing broilers were used in this experiment as a model. The chickens are randomly divided into four groups, each containing 25 individually caged chickens. Two groups were raised within environmental chambers maintained under continuous 32° C. and 80% relative humidity while the other two groups were in environmental chambers maintained at 24° C. and 60% relative humidity. The environmental chamber maintained at 32° C. constitutes the environmental heat stress while the chamber maintained at 24° C. the more ideal environmental temperature. Body weight gains, feed efficiency, and blood pH were monitored (TABLE VI).

TABLE VI

| | Body Weight Gain (g) | | Gain/Feed | | Non-Panting | |
|---|---|---|---|---|---|---|
| Treatment | TN 24° C. | Heat Stress 32° C. | TN 24° C. | Heat Stress 32° C. | TN 24° C. | Heat Stress 32° C. |
| 1. Standard Poultry Ration | $864^b$ | $407^c$ | .45 | .36 | 7.28 | 7.304 |
| 2. As 1 + .5% NaHCO$_3$ | $866^b$ | $444^c$ | .45 | .37 | 7.29 | 7.367 |
| Percent Desirable Improvement | +.2 | +9.1 | 0 | +2.8 | −.1 | −.9 |

$^b$Values within a major heading classification with unlike superscripts differ (P < .05).

The effects of sodium bicarbonate (0.5%) addition to a poultry ration on thermostressed chick growth are favorably reflected in weight gain and feed efficiency, but blood pH is adversely affected. Dietary addition of 0.5% NaHCO$_3$ increased (P<0.10) rate of gain by 9% and numerically increased feed efficiency. Blood pH of the panting heat stressed group did not differ (P=0.1) between the o and 0.5% NaHCO$_3$ levels though pH values for non-panting birds tended to increase (P<0.1) with NaHCO$_3$ addition. Any beneficial effects of NaHCO$_3$ on weight gain are due to the HCO$_3^-$ ion, independent of pH as alkalosis would not be favorably impacted by dietary HCO$_3^-$ (pk$_a$)=10.25). This positive gain response with NaHCO$_3$ confirms that which has been generally observed in the other experiments.

EXAMPLE VII

This experiment was conducted to evaluate HCO$_3^-$ and hydrogen ion donors for synergism in reducing the deleterious effect of heat stress. The birds, housing, environmental conditions and poultry rations were as described in EXAMPLE V with the exception that the experiment was conducted for three weeks. Results, (TABLE VII), demonstrate that the beneficial effects of including a hydrogen ion donor and HCO$_3^-$ in poultry rations are additive. And, like the previous EXAMPLE, the results indicate that dietary bicarbonate supplementation improves both gain and feed efficiency independent of any favorable effect upon blood pH.

TABLE VII

| | Body Weight Gain (g) | | Feed Consumption (g) | | | Blood pH Hot | |
|---|---|---|---|---|---|---|---|
| Treatment | TN 24° C. | Heat Stress 32° C. | TN 24° C. | Heat Stress 32° C. | TN 24° C. | Non-Panting 32° C. | Panting 32° C. |
| Basal Diet | $933^b$ | $442^d$ | $2617^b$ | $1949^c$ | $7.290^d$ | $7.294^d$ | 7.38 |
| Basal Diet + 1% NH$_4$Cl | — | $553^{dc}$ | — | $2173^c$ | — | $7.195^d$ | 7.30 |
| Basal + 1% NH$_4$Cl + .5% NaHCO$_3$ | — | $594^c$ | — | $2139^c$ | — | $7.276^d$ | 7.29 |

$^{bcd}$Values within a major heading classification with unlike superscripts differ (P < .05).

EXAMPLE VIII

This experiment was conducted to evaluated the potential of hydrogen ion donors and HCO$_3^-$ ions to reduce the mortality of poultry subject to acute (39° C., 74% relative humidity) heat stress. Treatments were replicated 6 times with 6 birds per replicate. Results, (TABLE VIII), demonstrate that acid supplementation dramatically reduces bird mortality while the bicarbonate ion increased mortality. Survival was inversely correlated (R=0.98) with blood pH suggesting that blood pH may be directly associated with bird mortaility.

TABLE VIII

| | Thermoneutral | | Heat Stressed | |
|---|---|---|---|---|
| | Mortality (%) | Blood pH | Mortality (%) | Blood pH |
| Poultry Ration | .0 | $7.29^a$ | $37.3^a$ | $7.443^a$ |
| Poultry Ration + .75% NaHCO$_3$ | .0 | $7.30^a$ | $44.5^a$ | $7.517^a$ |
| Poultry Ration + | .0 | $7.18^b$ | $3.4^b$ | $6.241^b$ |

TABLE VIII-continued

| | Thermoneutral | | Heat Stressed | |
|---|---|---|---|---|
| | Mortality (%) | Blood pH | Mortality (%) | Blood pH |
| 1% NH₄Cl | | | | |

$^{abc}$Means within a heading classification differ (P < .05).

EXAMPLE IX

Ten laying hens were fed a meal containing alkali to stimulate the blood alkalosis of heat stressed birds. Birds receiving the diet laced with 8% borax suffered from alkalosis and had reduced egg shell thickness similar to layers exposed to environmental heat stress. In view of this, hydrogen ion donors may be value to improve egg shell quality of layers exposed to environmental heat stress.

The hydrogen ion donor according to the present invention can generally be any acid or salt that hydrolyzes to provide an increase in the hydrogen ion concentration (i.e., the salts of a weak base and strong acid) as well known in the art provided in deleterious or toxic side effects are present. Thus, the hydrogen donor according to the present invention would include by way of example, but is not limited thereto; common consumable acids such as hydrochloric acid, citric acid, acetic acid, propionic acid, phosphoric acid and the like and consumable ammonium salts such as ammonium chloride, ammonium nitrate or other salts formed from weak bases and strong acids and the like. The sodium free bicarbonate ion donor according to the present invention can generally be any bicarbonate source that has a preponderance of cations other than sodium. The sources does not have to be pure calcium bicarbonate or the like, but preferably is to be predominantly sodium free. Thus, again by example, but not limited thereto, the sodium free bicarbonate ion donor would include calcium bicarbonate, potassium bicarbonate, magnesium bicarbonate and mixtures thereof.

In view of the novelty associated with the discovery and verification of specific chemical imbalances occurring during respiratory panting of poultry and subsequent novelty associated with the discovery that the deleterious effects of these chemical imbalances can be alleviated by dietary changes, the present invention in the broadest sense encompasses any food or water additive that can temporarily induce the desired change in the blood pH of the fowl. Thus, any additive or supplement, drug or the like that repartitions poultry metabolism inducing the desired increase in blood acidity is contemplated as being equivalent for purposes of treating heat stress in birds. Thus, the concept of introducing a hydrogen blocker or hydrogen antagonist such as the exemplified cimetidiene is felt to be equivalent for purposes of this invention. Also, it is felt that agents or additives that result in ketosis (although generally considered as being undesirable) for purposes of treating or alleviating the effects of heat stress according to the present invention is desirable and useful. Thus, the concept of intentionally subjecting the birds to massive quantities of protein (protein toxicity) or the use of other known ketosis inducing substances such as acetoacetic adid or β hydroxybutyric acid to temporarily reduce blood pH is also felt to be within the scope of the present invention. In other words, the novelty associated with the present invention furthwr involves recognition that the chemical imbalances produce such drastic changes in the rate of growth, shell thickness and mortality rate that the use of feed or water supplements and the use of metabolic interfering processes that would in thermoneutral conditions to be considered deleterious are in these circumstances appropriate.

EXAMPLE X

In order to study interactions between growth rate, mortality, ambient temperature, blood pH and the potassium requirement of poultry, a series of six experiments were conducted. During each experiment, Arbor Acre×Vantress chicks were raised on rice hull litter and fed a corn soybean meal starter diet during the first 3 weeks posthatching. On the first day of the 4th week, following an overnight fast, chicks were sexed, weighed and randomly allotted to treatment such that each treatment contained 10 replicates of 8 chicks (4 male, 4 female) per replicate. Birds were housed in wire floored grower batteries containing 51×82 cm compartments within thermostatically and humidistatically controlled chambers under continuous tungsten filament lighting. Week 4 was utilized to adapt all birds to test rations of Table IX and to increase chamber temperature (2.8 C./day) to 35° C. (70% relative humidity) while controls were maintained under more ideal conditions of 24° C. (65% relative humidity). Feed and water were continuously available. Body weight gains and feed consumption were tallied weekly. All KCl, $K_2CO_3$ and NH₄Cl supplementations were added to the birds' drinking water. Previous observations made in the laboratory indicated that heat stressed broilers increased live weight gain when their drinking water contained 0.3% NH₄Cl. Where blood data are reported, blood was obtained via jugular venipuncture and pH immediately determined utilizing a Corning blood pH/gas analyzer. All data were subjected to analysis of variance using the General Linear Model of the statistical analysis system (Barr et al, "A Users Guide to SAS", Statistical Analysis System Institute, Inc., Carry, N.C., 1976). Duncan's multiple range tests were used to determine differences (P<0.05) between means when a significant F statistic was indicated by the analysis of variance (Steel et al, "Principles and Procedures of Statistics", McGraw-Hill Book Co., N.Y, 1960). Correlation coefficients where reported were estimated as specified by Steel et al (1960).

TABLE IX

| Composition of Basal Ration | | |
|---|---|---|
| Ingredient | Numerical Name[1] | % |
| Ground Corn | 4-02-931 | 57 |
| Soybean Meal (44%) | 5-04-604 | 22 |
| Fish Meal (Menhaden) | 5-02-009 | 9 |
| Tallow | | 5 |
| Ground Alfalfa | 1-00-023 | 2.7 |
| Dicalcium Phosphate | 6-01-080 | 2.5 |
| Calcium Carbonate | 6-01-069 | .9 |
| Vitamin Mix | — | .4 |
| Salt | 6-14-013 | .3 |
| Trace Mineral Mix | — | .1 |
| D-L-Methionine | — | .1 |

[1]Atlas of Nutritional Data on United States and Canadian Feeds

In experiment 1, the basal ration was tested for potassium adequacy in this 2 week study. Broilers received 0, 0.05, 0.1 and 0.15% supplemental potassium (weight percent based on weight of additional potassium; hereinafter referred to as K).

In experiment 2, the occurrence of any interaction between NH₄Cl and KCl supplementation was evaluated. Treatments were arranged in a 4×4 factorial. Ammonium chloride levels examined include 0, 0.1, 0.2, 0.3% and KCl levels included, 0, 0.05, 0.1, 0.15. Parameters evaluated include body weight gain, feed efficiency and blood pH.

In experiment 3, the effects of the K supplement anion composition on body weight gain, feed efficiency and blood pH were evaluated. Broilers were supplemented with isomolar quantities of KCl and KCO$_3$ supplying the chicks with 0.2% K from each source.

In experiment 4, the NH$_4$Cl/KCl interaction was further refined. Parameters evaluated include body weight gain, feed efficiency and blood pH.

In experiment 5, efficacy of NH$_4$Cl, NaHCO$_3$ and ascorbic acid additions to drinking water containing 0.15% K were evaluated. The evaluation lasted 3 weeks with live weight gain and feed efficiency being monitored.

In experiment 6, the relationship between mortality of birds exposed to acute heat stress (e.g., 38.3 C., 52% relative humidity) for 2 hours was examined. Broilers received 0, 0.2, 0.4 and 0.6% K. Potassium levels 0 and 0.6% were replicated 16 times while the 0.2 and 0.4% supplemental levels had 14 replications. All replicates contained 5 birds each. The experiment was then repeated for similar acute heat stress conditions at varying levels of thermal conditioning.

The test ration utilized throughout this study was evaluated in the first experiment for potassium adequacy in broilers reared within a thermoneutral environment and the resulting data are presented in Table X. Supplementing chicks with 0.05, 0.10 and 0.15% K did not impact (P22 0.10) either body weight gain or feed efficiency. A K response was not expected as the test ration contained 0.76 K and the chick's requirement has been estimated to be just 0.2% (National Research Council).

TABLE X

| Broiler Weight Gain and Feed Efficacy | | | | |
|---|---|---|---|---|
| | % Supplemental K | | | |
| | 0 | .05 | .10 | .15 |
| Gain (g) | 1157.5 | 1121.7 | 1200.6 | 1077.9 |
| Gain/Feed | .37 | .37 | .38 | .35 |

In the second experiment, the effects of tap water supplemented with KCl and NH$_4$Cl on growth rate, blood pH and feed efficiency were evaluated in chicks housed within the chronically heat stressed environment. The resulting data are presented in Table XI. Broilers consuming the test ration and untreated tap water had an average panting pH of 7.45. Data presented by Hurwitz et al, "Sodium and Chloride Requirements of the Chick; Relationship to Acid-Base Balance", Poultry Sci., 52: 903–909, 1973) correlating live weight gain with blood pH, indicated that optimal growth rate occurred at a blood pH of 7.28, that growth rate declined markedly at pH values exceeding 7.30 and moderately at pH values falling between 7.20 and 7.15. Similarly work conducted by the present inventor indicated that panting blood pH values exceeding 7.35, precipitated by environmental stress result in reduced broiler growth rate and feed consumption. In this experiment, supplementing the drinking water of heat stressed chicks with 0.3% NH$_4$Cl reduced blood pH to 7.33 and increased (P<0.10) live weight grain by 7.2%. Supplementing drinking water with 0.4 and 0.5% NH$_4$Cl reduced panting phase pH to 7.25 and 7.17, decreased body weight gain by 3.1 and 22.3%, respectively, and likely precipitated non-panting phase acidosis. It was observed that panting phase blood pH values falling below 7.28 are generally associated with non-panting phase acidosis and a decreased body weight gain for chicks exposed to heat stress. Use of ammonium chloride to combat heat stress appears efficacious, but caution must be utilized to avoid precipitating toxicity via non-panting phase acidosis. Based on this experiment, optimal NH$_4$Cl supplementation level is preferably 0.3% or less.

Adding 0.5, 0.1, and 0.15 K as KCl to broiler drinking water (again see Table XI) resulted in a linear (P<0.01) increase in live weight grain. However, KCl supplementation failed to impact (P>0.10) blood pH. Apparently, blood pH is important only when K intake is insufficient for maximal growth rate. A significant interaction (P<0.01) existed between KCl and NH$_4$Cl supplementation. As the drinking water KCl supplementation level increased, toxicity of the 0.4 and 0.5% NH$_4$Cl levels was exacerbated. The significant interaction existing between KCl and NH$_4$Cl suggests the K$^+$ and H$^+$ ions are indeed related through metabolism. However, Cl$^-$ contributions to growth could not be ruled out.

TABLE XI

| Broiler Weight Gain, Feed Efficiency and Blood pH Values | | | | |
|---|---|---|---|---|
| % | | | | |
| K(KCl) | NH$_4$Cl | Gain (g) | Gain/Feed | Blood pH |
| 0 | 0 | 376.9$^{efg}$ | .29$^a$ | 7.45$^a$ |
| 0 | .3 | 403.0$^{cde}$ | .31$^a$ | 7.33$^{bc}$ |
| 0 | .4 | 387.6$^{def}$ | .27$^a$ | 7.25$^{cdc}$ |
| 0 | .5 | 352.3$^{fg}$ | .29$^a$ | 7.17$^{efg}$ |
| .05 | 0 | 389.2$^{def}$ | .30$^a$ | 7.39$^{ab}$ |
| .05 | .3 | 452.7$^{ab}$ | .32$^a$ | 7.27$^{cd}$ |
| .05 | .4 | 399.7$^{cde}$ | .29$^a$ | 7.23$^{dc}$ |
| .05 | .5 | 344.3$^b$ | .27$^a$ | 7.14$^{fgh}$ |
| .1 | 0 | 416.5$^{bcd}$ | .30$^a$ | 7.41$^{ab}$ |
| .1 | .3 | 456.6$^{ab}$ | .29$^a$ | 7.27$^{cd}$ |
| .1 | .4 | 431.7$^{bc}$ | .32$^a$ | 7.19$^{def}$ |
| .1 | .5 | 303.8$^h$ | .25$^a$ | 7.16$^{fg}$ |
| .15 | 0 | 444.6$^b$ | .31$^a$ | 7.40$^{ab}$ |
| .15 | .3 | 484.7$^a$ | .31$^a$ | 7.17$^{efg}$ |
| .15 | .4 | 358.5$^{fg}$ | .27$^a$ | 7.09$^{gh}$ |
| .15 | .5 | 263.6$^i$ | .18$^b$ | 7.07$^h$ |

$^{abcdefghi}$Means within a column with unlike superscripts differ (P < .05).

Chloride efficacy was compared with CO$_3{}^{--}$ in the third experiment by contrasting equimolar supplementation levels of KCl and KCO$_3$ in heat stressed chicks. The resulting data are presented in Table XII. Both KCl and K$_2$CO$_3$ increased (P<0.05) weight gain of the thermostressed chicks similarly. Lack of a significant difference between KCl and K$_2$CO$_3$ indicates that the effect is most likely mediated by K as CO$_3{}^{--}$ is basic. A similar trial of NaCl showed no effect.

TABLE XII

| Broiler Weight Gain and Feed Efficiency Values | | |
|---|---|---|
| Ration | Gain (g) | Gain/Feed |
| Basal | 445.5$^b$ | .27 |
| Asl + .15% K as KCl | 561.8$^a$ | .31 |
| Asl + .15% K as K$_2$CO$_3$ | 552.2$^a$ | .30 |

$^{ab}$Means within column with unlike superscripts differ (P < .05).

The KCl/NH$_4$Cl interaction was evaluated at lower NH$_4$Cl supplementation levels in the fourth experiment and the resulting data are presented in Table XIII. Ammonium chloride levels evaluated included 0.1, 0.2 and 0.3%. Like the second experiment, NH$_4$Cl addition to the heat stressed chicks' drinking water enhanced live weight gain and depressed blood pH. However, the NH$_4$Cl effect on live weight gain was maximized at the 0.2% supplementation level. As in experiment 2, KCl enhanced live weight gain and the KCl/NH$_4$Cl interaction was significant (P<0.01).

TABLE XIII

Broiler Weight Gain, Feed Efficiency and Blood pH Values

| % | | | |
|---|---|---|---|
| K | NH$_4$Cl | Gain (g) | Blood pH |
| 0 | 0 | 190.3$^c$ | 7.47$^a$ |
| 0 | .1 | 217.3$^{de}$ | 7.37$^{bcd}$ |
| 0 | .2 | 233.4$^{cde}$ | 7.35$^{bcde}$ |
| 0 | .3 | 221.4$^{de}$ | 7.25$^f$ |
| .05 | 0 | 220.8$^{de}$ | 7.40$^{abc}$ |
| .05 | .1 | 212.0$^{de}$ | 7.37$^{bcd}$ |
| .05 | .2 | 246.8$^{abcd}$ | 7.35$^{bcde}$ |
| .05 | .3 | 241.9$^{bcd}$ | 7.32$^{cdef}$ |
| .1 | 0 | 228.1$^d$ | 7.41$^{abc}$ |
| .1 | .1 | 236.1$^{cd}$ | 7.42$^{ab}$ |
| .1 | .2 | 274.3$^{ab}$ | 7.36$^{bcde}$ |
| .1 | .3 | 223.7$^{de}$ | 7.27$^f$ |
| .15 | 0 | 279.3$^a$ | 7.42$^{ab}$ |
| .15 | .1 | 266.7$^{abc}$ | 7.38$^{bc}$ |
| .15 | .2 | 275.1$^{ab}$ | 7.36$^{bcde}$ |
| .15 | .3 | 236.6$^{cd}$ | 7.28$^{def}$ |

$^{abcdef}$Means within a column with unlike superscripts differ (P < .05).

Data confirming the beneficial effects of adding NH$_4$Cl, NaHCO$_3$ and ascorbic acid to the 0.15% K drinking water tended (P<0.1) to enhance live weight gain are presented in Table XIV. The additives resulted in less variation and a more enhanced performance.

TABLE XIV

Broiler Weight Gains

| Supplement | Gain (g) |
|---|---|
| None | 445$^b$ |
| .2 K | 530$^a$ |
| .2 K + .04 NaHCO$_3$ + 1000 ppm Ascorbic Acid | 549$^a$ |

The impact of KCl supplementation on broilers exposed to acute heat stress was examined in experiment 6 and the data corresponding to separate testing are presented in Table XV. Potassium chloride effects upon death losses of the heat stressed poultry were striking. Addition of potassium chloride to the birds' drinking water resulted in a significant (P<0.05) dose dependent reduction in death loss. Overall, K addition at the 0.6% level decreased death losses by 83%.

Data reported herein substantiate acid/base balance of chronically heat stressed broilers as a growth rate limiting factor and establishes the interaction between K+ and H+. Level of K needed by the stressed birds are 8 to 15 times the accepted daily requirement.

TABLE XV

Mortality Data #2

| | Mortality (%) | |
|---|---|---|
| Supplemental K (%) | Males | Females |
| 0 | 20$^a$ | 22$^a$ |
| .2 | 15$^{ab}$ | 25$^a$ |
| .4 | 3$^b$ | 12$^b$ |
| .6 | 1$^b$ | 6$^b$ |

$^{ab}$Means within a column with unlike superscripts differ (P < .05). 38.3 C; 52% relative humidity after birds were maintained at low 26.7 C cycled to high 36.7 C for 3 weeks prior to test. 8 replicates of 6 birds per replicate for each sex.

Mortality Data #3

TABLE XV-continued

| | Mortality | |
|---|---|---|
| K % | Males | Females |
| 0 | 56.3$^a$ | 62.5$^a$ |
| .2 | 44.6$^a$ | 66.1$^a$ |
| .4 | 42.8$^a$ | 67.8$^a$ |
| .6 | 21.8$^b$ | 28.1$^b$ |

$^{ab}$Means within a column with unlike superscripts differ (P < .05). 40 C; 55% relative humidity after birds were maintained at low 26.7 C cycled to high 36.7 C for 7 days prior to test. 8 replicates of 5 birds per replicate for each sex.

Mortality Data #4

| K % | Males | Females |
|---|---|---|
| 0 | 89.3 | 88.7 |
| .4 | 66.1 | 86.6 |
| .6 | 32.1 | 31.2 |
| .8 | 30.4 | 23.2 |

38.3 C; 55% relative humidity after birds were maintained at 26.7 C cycled to 32.2 C for 3 days prior to test. 8 replicates with 8 birds per replicate for each sex.

To further test the efficacy of administering supplemental potassium under field simulated conditions during potential periods of heat stress for purposes of improving weight gain, 20 replicates of 6 birds per replicate were tested. Again, the feed composition of Table IX was employed in combination with supplemental KCl addition to the poultry drinking water. The study was performed for 24 days with cycling temperatures from a low of 26.7° C. to a high of 36.7° C. The resulting data is presented in Table XVI.

TABLE XVI

Broiler Weight Gain

| Supplemental K (%) | Gain (g) |
|---|---|
| 0 | 822 |
| .12 | 838 |
| .18 | 837 |
| .24 | 881 |
| .30 | 921 |
| .36 | 888 |

Cycling temperature study low = 26.7 C; high = 36.7 C 20 replicates of 6 birds per replicate From the composite of the above experiments and resulting data, the acceptable concentration range for supplemental potassium in the poultry drinking water for optimum growth is preferably from about 0.05% K up to about 0.3% K while the preferred range for enhancing mortality may go as high as 1.0% K per unit mass drinking water. Similarly, the acceptable concentration range for supplemental ammonium chloride in the poultry drinking water for optimum growth is preferably about 0.10% NH$_4$Cl up to about 10.3% NH$_4$Cl, while the preferred range for enhancing mortality may go as high as about 0.6% NH$_4$Cl per unit mass of water. These concentration ranges seem to be characteristic of mixtures of potassium and NH$_4$Cl; however, it should be kept in mind that the risk of exceeding the upper limit on the NH$_4$Cl mortality range may be more serious than that of exceeding the upper range of the KCl. As such, it is preferred that when blends of KCl/NH$_4$Cl are to be employed, the potassium salt is preferably the major component. Further, in view of the testing of the sodium bicarbonate and ascorbic acid, it is felt that a beneficial effect for growth is achieved when about 0.0005NaHCO$_3$ up to about 0.1% NaHCO$_3$ is present per unit mass of water and at least some ascorbic acid is present. It should be appreciated that the administration of supplemental potassium during heat stress can best be performed by employing a water administration system, however, the actual additive can be conveniently manufactured and distributed in the form of a blend of dry powders. Preferably, the concentrated additive will have 40 to 100 parts by weight potassium salts such as KCl or the like and up to 15 parts by weight $NH_4Cl$; up to about 18 parts by weight $NH_4HCO_3$ and ascorbic acid. One particular preferred dry powder additive to be added to the poultry drinking water is presented in Table XVII.

TABLE XVII

| Additive | Weight % |
|---|---|
| KCl | 94.5 |
| $NH_4Cl$ | 3.0 |
| $NH_4HCO_3$ | 2.0 |
| Ascorbic acid | 0.5 |

Preferably, the above additive is added to the poultry drinking water by dispensing a prepared concentration solution through a thermostatically regulated medicator. For example, the medicator can be preferably set at 85° F. such as to deliver approximately 3 ounces of concentrate per gallon of drinking water. In such an application, approximately 26.75 pounds ($\simeq$12.12 Kg) of the concentrate such as illustrated in Table XVII is thoroughly dissolved in approximately 25 gallons of water and then placed in the medicator holding tank for dispensing into the poultry drinking water whenever the preset temperature is exceeded. It should be appreciated that other concentrations and dosage rates can be readily employed generally consistent with the exemplified preferred rates.

Thus, in summary, the actual method of administering the additive to the poultry can be essentially by any method or technique well known in the art, including incorporating the additive into the feedstuff or water or both. Preferably, the overall dosage rates as previously expressed in terms of a weight percentage range represent the total of the supplement (whether supplied by feedstuff or water) as a function of the weight of the feedstuff consumed by the bird, except for the water administration examples which are expressed as a function of the weight of water. Feed dosages need to be multiplied by 10 or more to equal the intake achieved by water administration as water intake during stress will exceed feed intake dramatically. It should also be appreciated that the previously identified hydrogen ion donor range is specified in terms of the exemplified ammonium chloride and although considered characteristic of most additives, the upper and lower limits can vary somewhat when the specific molecular weight of the additive is taken into consideration. Thus, the preferred 1 weight percent ammonium chloride is equivalent to about 0.68 weight percent hydrochloric acid and for other higher molecular weights the optimum value as well as the upper and lower limits can be further adjusted. It should also be appreciated that the preferred concentration or dosage rate will vary according to the severity of the heat stress. Thus, water administration represents a particularly attractive method of introducing the desired additive or supplement into the diet of the bird in that the desired amount can be varied from moment to moment. In this manner, the additive concentration can be changed as the temperature varies from day to day or even from daylight to nighttime and the like. This has the added advantage of reducing additive wastage. In the water administration technique, the previous weight ratio of the hydrogen ion donor ($NH_4Cl$) can be expressed as a weight percent hydrogen ion introduced per unit mass of feedstuff consumed (i.e., about 0.0056 to about 0.056 weight percent). In such water management applications, the environment can be continuously monitored and appropriate rate of acid can be added to the water according to the feed rate of the poultry involved. Such a system, in principle, can be totally automated.

The advantages of using the dietary additives and processes of the present invention are numerous. In addition to the ease of application, control and monitoring of results, implementing the present invention results in improved rate of growth during periods of heat stress wherein the rate of growth is severely inhibited. The present invention further results in improvements in the mortality rate during periods of chronic and acute heat stress as well as improving egg shell thickness during similar heat stress periods. Inasmuch as the number of birds surviving to market is increased, the feed efficiency will also be enhanced. Consequently, the present invention provides significantly increased feed efficiency and overall improved economics for the poultry industry.

Having thus described the invention with a certain degree of particularity, it is to be understood that the invention is not limited to the embodiments set forth herein for purposes of exemplification, but is to be limited only by the scope of the attached claims, including a full range of equivalents to which each element thereof is entitled.

I claim:

1. A method of treating heat stress in poultry comprising the step of supplementing the diet of said poultry with poultry drinking water containing from about 0.05 weight percent to about 1.0 weight percent dissolved potassium ion.

2. A method according to claim 1 for treating heat stress in poultry and which further enhances the rate of growth wherein the weight percent of dissolved potassium ion is about 0.24.

3. A method of claim 2 wherein the dissolved potassium ion is potassium chloride.

4. A method of claim 2 wherein the dissolved potassium ion is potassium carbonate.

5. A method of treating heat stress in poultry comprising the step of supplementing the diet of said poultry with poultry drinking water containing from about 0.05 weight percent to about 1.0 weight percent of at least one water soluble, non-toxic, potassium salt.

6. A method of claim 5 wherein said water soluble potassium salt is present in from 40 to 100 parts by weight for every 100 parts by weight of total dissolved salts.

7. A method of claim 5 wherein said poultry drinking water further contains from about 0.0005 weight percent to about 0.1 weight percent dissolved $NH_4HCO_3$.

8. A method of claim 7 wherein said poultry drinking water further contains dissolved ascorbic acid.

9. A poultry drinking water additive comprising for every 100 parts by weight of the additive:
   (a) from about 40 to about 99 parts by weight of a water soluble, non-toxic, potassium salt;
   (b) up to about 15 parts by weight $NH_4Cl$;
   (c) up to about 18 parts by weight $NH_4HCO_3$; and
   (d) the balance, ascorbic acid.

10. A poultry drinking water additive of claim 9 comprising about 94.5 parts by weight non-toxic potassium salt. about 3 parts by weight $NH_4Cl$, about 2 parts by weight $NH_4HC_3$ and about 2 parts by weight ascorbic acid.

11. A method of claim 5 wherein in addition to the potassium salt, there is present $NH_4Cl$ and wherein the weight percent is based on the weight of potassium plus the weight of $NH_4Cl$ per unit mass of water.

* * * * *